United States Patent
Proksa (10) Patent No.: US 9,405,018 B2
(45) Date of Patent: Aug. 2, 2016

(54) RADIOGRAPHIC APPARATUS FOR DETECTING PHOTONS WITH OFFSET CORRECTION

(71) Applicant: KONINKLIJKE PHILIPS N.V., Eindhoven (NL)

(72) Inventor: Roland Proksa, Neu Wulmstorf (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 127 days.

(21) Appl. No.: 14/351,892

(22) PCT Filed: Oct. 5, 2012

(86) PCT No.: PCT/IB2012/055362
§ 371 (c)(1),
(2) Date: Apr. 15, 2014

(87) PCT Pub. No.: WO2013/061186
PCT Pub. Date: May 2, 2013

(65) Prior Publication Data
US 2014/0328464 A1    Nov. 6, 2014

Related U.S. Application Data (60) Provisional application No. 61/551,465, filed on Oct. 26, 2011.

(51) Int. Cl.
*G01T 1/17* (2006.01)
*G01N 23/04* (2006.01)

(52) U.S. Cl.
CPC ...... *G01T 1/17* (2013.01); *G01N 23/04* (2013.01); *G01N 23/046* (2013.01); *G01N 2223/419* (2013.01)

(58) Field of Classification Search
CPC ........... G01T 1/17; G01T 1/2928; G01T 7/00; G01N 23/04; G01N 23/046; G01N 23/06; G01N 23/08; G01N 23/083; G01N 23/087; A61B 6/4241; A61B 6/482; A61B 6/585
USPC ......... 378/19, 62, 98.8, 98.9, 207; 250/336.1, 250/395
See application file for complete search history.

(56) References Cited

U.S. PATENT DOCUMENTS

| 4,058,728 A | 11/1977 | Nickles |
| 5,012,498 A | 4/1991 | Cuzin et al. |

(Continued)

FOREIGN PATENT DOCUMENTS

| EP | 2237550 A2 | 10/2010 |
| WO | 2006/064403 | 6/2006 |

OTHER PUBLICATIONS

Llopart, X., et al.; Medipix2: a 64-k Pixel Readout Chip With 55-um Square Elements Working in Single Photon Counting Mode; 2002; IEEE Trans. on Nuclear Science; 49(5)2279-2283.

(Continued)

*Primary Examiner* — Jurie Yun (57) ABSTRACT

A detection apparatus for detecting photons, such as used in radiographic imaging systems includes a detection unit that generates detection signal pulses having a detection signal pulse height being indicative of the energy of the detected photons, a detection values generation unit that generates energy-resolved detection values depending on the detection signal pulses and a signal pulse generation unit that generates artificial signal pulses having a predefined artificial signal pulse height and a predefined generated rate. The detection values generation unit determines an observed rate of the artificial signal pulses having an artificial signal pulse height being larger than a predefined threshold as observed by the detection values generation unit and determines an offset of the detection signal pulses depending on the determined observed rate. This allows reliably determining the offset of the detection signal pulses, which can be used for correcting the finally generated detection values.

19 Claims, 4 Drawing Sheets

(56) References Cited

U.S. PATENT DOCUMENTS

| | | |
|---|---|---|
| 6,797,960 B1 | 9/2004 | Spartiotis et al. |
| 2006/0188061 A1 | 8/2006 | Takenaka et al. |
| 2009/0238330 A1 | 9/2009 | Luhta et al. |
| 2009/0290050 A1 | 11/2009 | Herrmann et al. |
| 2010/0329425 A1 | 12/2010 | Guo et al. |

OTHER PUBLICATIONS

Roessl, E., et al.; K-edge imaging in x-ray computed tomography using multi-bin photon counting detectors; 2007; Phys. Med. Biol.; 52:4679-4696.

Takahashi, T., et al.; Recent Progress in CdTe and CdZnTe Detectors; 2000; IEEE Trans. on Nuclear Science; 48(4)950-959.

RADIOGRAPHIC APPARATUS FOR DETECTING PHOTONS WITH OFFSET CORRECTION

CROSS REFERENCE TO RELATED APPLICATIONS

This application is a national filing of PCT application Ser. No. PCT/IB2012/055362, filed Oct. 5, 2012, published as WO 2013/061186 A1 on May 2, 2013, which claims the benefit of U.S. provisional application Ser. No. 61/551,465 filed Oct. 26, 2011, which is incorporated herein by reference.

FIELD OF THE INVENTION

The invention relates to a detection apparatus, a detection method and a detection computer program for detecting photons. The invention relates further to an imaging apparatus, an imaging method and an imaging computer program for imaging an object.

BACKGROUND OF THE INVENTION

The article "Medipix2: A 64-k pixel readout chip with 55-µm square elements working in single photon counting mode" by X. Llopart et al., IEEE Transactions on Nuclear Science, volume 49, issue 5, pages 2279 to 2283, October 2002 discloses a photon counting detector, which generates detection values depending on detected photons. In particular, a direct conversion material is used for transforming photons into signal pulses, wherein each signal pulse corresponds to a single photon and wherein the signal pulse height of the respective signal pulse is indicative of the energy of the respective photon. The signal pulses are distributed among several energy bins, wherein for each energy bin a detection value is generated, which is indicative of the rate of signal pulses assigned to the respective energy bin.

The signal pulse height can comprise an offset caused by persistent currents. This offset may lead to a corrupted distribution of the signal pulses among the energy bins and, thus, to a reduced quality of the generated detection values.

SUMMARY OF THE INVENTION

It is an object of the present invention to provide a detection apparatus, a detection method and a detection computer program for detecting photons, which allow reliably determining the offset. It is a further object of the present invention to provide an imaging apparatus, which comprises the detection apparatus, and a corresponding imaging method and imaging computer program for imaging the object.

In a first aspect of the present invention a detection apparatus for detecting photons is presented, wherein the detection apparatus comprises
- a detection unit for detecting photons, wherein the detection unit is adapted to generate detection signal pulses having a detection signal pulse height being indicative of the energy of the respective detected photon,
- a detection values generation unit for generating energy-resolved detection values depending on the detection signal pulses,
- a signal pulse generation unit for generating artificial signal pulses having a predefined artificial signal pulse height and a predefined generated rate and for providing the generated artificial signal pulses to the detection values generation unit, wherein the detection values generation unit is adapted to a) receive the artificial signal pulses, b) determine an observed rate being the rate of the received artificial signal pulses having an artificial signal pulse height being larger than a predefined artificial signal height pulse threshold, wherein the artificial signal height pulse threshold is similar or larger than the predefined artificial signal pulse height, and c) determine an offset of the detection signal pulses depending on the determined observed rate of the artificial signal pulses.

Since the artificial signal height threshold is similar to or larger than the predefined artificial signal pulse height, the observed rate should be very small or zero, if an offset is not present, while determining the observed rate. With increasing offset also the observed rate will increase, because, due to the offset, the artificial signal pulse heights will be larger than originally generated such that more artificial signal pulses have artificial signal pulse heights being larger than the predefined artificial signal height threshold. The observed rate is therefore a reliable measure for the offset of the artificial signal pulses received by the detection values generation unit and, thus, for the offset of the detection signal pulses. The offset of the detection signal pulses can therefore reliably be determined depending on the determined observed rate of the artificial signal pulses.

The detection unit comprises preferentially a direct conversion material like cadmium cerium (CdCe) or cadmium zinc telluride (CZT) for generating the detection signal pulses depending on photons meeting the direct conversion material.

The detection values generation unit is preferentially adapted to compare the artificial signal pulses with the artificial signal height pulse threshold for determining the observed rate. The detection values generation unit is preferentially further adapted to compare the detection signal pulses with detection signal height pulse thresholds defining energy bins, in order to distribute the detection signal pulses among the energy bins, wherein for each energy bin a detection value is determined being indicative of the rate of detection signal pulses assigned to the respective energy bin. The comparison procedures for comparing the detection signal pulses and the artificial signal pulses with respective thresholds are preferentially performed by comparators of the detection values generation unit.

The observed rate is preferentially the rate of artificial signal pulses having an artificial signal pulse height larger than the artificial signal height pulse threshold, when the artificial signal pulse heights are compared with the artificial signal height pulse threshold in the detection values generation unit. The generated rate refers to a respective rate as generated by the signal pulse generation unit.

It is preferred that the detection signal pulse heights are smaller than a predefined maximal detection signal pulse height, wherein the artificial signal height pulse threshold is larger than the maximal detection signal pulse height. This ensures that only artificial signal pulses contribute to the observed rate and not detection signal pulses, thereby further improving the reliability of determining the offset.

It is further preferred that the detection values generation unit comprises assignments between observed rates and the offsets, wherein the detection values generation unit is adapted to determine the offset based on the assignments and the actual observed rate. The assignments can be determined by calibration measurements, wherein the observed rate is determined, while the offset and the predefined generated artificial signal pulses are known, i.e. their generated artificial signal pulse heights and the generated rate. The assignments can also be provided as a function between the observed rate and the offset, which can be based on theoretical considerations.

In particular, the detection values generation unit can be adapted to i) provide a model modeling the observed rate as a product of a) the generated rate of artificial signal pulses and b) a noise likelihood defining the likelihood that the noise in the artificial signal pulses is larger than the artificial signal height pulse threshold minus a generated artificial pulse height and minus the offset, and ii) modify the offset to be determined such that deviations between the modeled observed rate and an actual observed rate are reduced, thereby determining the offset. The noise likelihood is preferentially provided by a noise likelihood function. The noise in the artificial signal pulses is a random fluctuation of the artificial signal pulses being an electronic noise which is a characteristic of the detection apparatus, in particular, of the detection values generation unit.

The likelihood can be determined by integrating a corresponding likelihood density like a Gaussian likelihood density from a) the artificial signal height pulse threshold minus a generated artificial pulse height and minus the offset to b) infinity. This allows determining the offset very accurately based on the assumption that, when comparing the artificial signal pulse height with the artificial signal pulse height threshold, the artificial signal pulse height is a combination of the original artificial signal pulse height as predefined and generated by the signal pulse generation unit, noise and the offset.

The detection values generation unit can be adapted to provide a pile-up model modeling a pile-up effect caused by combined detection signal and artificial signal pulses having a combined signal pulse height being larger than the artificial signal height pulse threshold and to correct the observed rate of artificial signal pulses being larger than the artificial signal height pulse threshold based on the pile-up model.

In an embodiment, the detection values generation unit is adapted to generate the energy-resolved detection values by comparing the detection signal pulses with detection signal height pulse thresholds defining energy bins, in order to distribute the detection signal pulses among the energy bins, and to correct the distribution of detection signal pulses based on the offset, thereby generating for each energy bin a corrected detection value being indicative of the rate of detection signal pulses of the respective energy bin. This allows improving the quality of the detection values by correcting the distribution among the energy bins for the offset.

Preferentially, the detection values generation unit is adapted to determine a sensitivity of a rate of detection signal pulses assigned to an energy bin on the offset and to correct the rate of detection signal pulses assigned to the energy bin based on the offset and the determined sensitivity. The consideration of the sensitivity of the rate of detection signal pulses assigned to an energy bin on the offset while correcting this rate further improves the quality of the detection values.

It is further preferred, that the energy bin is defined by two detection signal pulse thresholds, a first detection signal pulse threshold and a second detection signal pulse threshold, wherein the detection values generation unit is adapted to determine the rate of detection signal pulses of an energy bin as the difference between a) a first rate being the rate of detection signal pulses having detection signal pulse heights being larger than the first detection signal height pulse threshold and b) a second rate being the rate of detection signal pulses having detection signal pulse heights being larger than the second detection signal height pulse threshold, determine a third rate being the rate of detection signal pulses having a detection signal pulse height being larger than a first sensitivity signal height pulse threshold, which is smaller than the first detection signal pulse height threshold, determine a fourth rate being the rate of detection signal pulses having detection signal pulse heights being larger than a second sensitivity signal pulse height threshold, which is smaller than the second detection signal pulse height threshold, determine the sensitivity of the rate of detection signal pulses assigned to the energy bin on the offset depending on a difference between the first and third rates and a difference between the second and fourth rates.

The offset of a detection signal pulse height can be considered by assuming that the detection signal pulse height has not been modified by the offset, but that the detection signal pulse height thresholds defining the respective energy bin have been correspondingly moved. Thus, the difference between the first and third rates is indicative of the sensitivity of the rate of the detection signal pulses assigned to the respective energy bin on a movement of the first detection signal pulse height threshold caused by the offset and the difference between the second and fourth rates is indicative of the sensitivity of the rate of the detection pulse signals assigned to the respective energy bin on a movement of the second detection signal pulse height threshold due to the offset. If the difference between the first and third rates and the difference between the second and fourth rates are subtracted from each other, the subtraction result is indicative of the change of the rate of the detection signal pulses assigned to the respective energy bin, if an offset is present. This subtraction result can therefore be regarded as being the sensitivity of the rate of detection signal pulses assigned to the respective energy bin on the offset.

In an embodiment, the detection values generation unit can be adapted to determine the sensitivity of a rate of detection signal pulses assigned to a respective energy bin on the offset based on an average of a) a ratio of the rate of detection signal pulses assigned to the respective energy bin to the width of the respective energy bin and b) a ratio of the rate of detection signal pulses assigned to an adjacent energy bin to the width of the adjacent energy bin. This allows determining the sensitivity only based on comparisons of the detection signal pulse heights with the detection signal pulse height thresholds defining the energy bins, without necessarily requiring a comparison with a further threshold like the above mentioned sensitivity signal height thresholds. In particular, for a respective energy bin, a first average can be determined, which is the average between a) a ratio of the rate of detection signal pulses assigned to the respective energy bin to the width of the respective energy bin and b) a ratio of the rate of detection signal pulses assigned to the immediately previous energy bin to the width of the immediately previous energy bin, and a second average can be determined, which is an average of a) a ratio of the rate of the detection signal pulses assigned to the respective energy bin to the width of the respective energy bin and b) a ratio of the rate of detection signal pulses assigned to an immediately following energy bin to the width of the immediately following energy bin. The sensitivity for the respective energy bin can be determined by subtracting the first and second averages from each other.

The detection values generation unit can be adapted to correct the rate of detection signal pulses assigned to a respective energy bin based on a product of the offset and the sensitivity of the rate of detection signal pulses assigned to the respective energy bin on the offset. This allows correcting the detection values in a relatively simple way. In particular, for an energy bin the product of the offset and of the sensitivity can be added to the rate of detection pulse signals assigned to the energy bin, in order to correct the respective detection value.

The detection values generation unit can also be adapted to generate the energy-resolved detection values by a) correcting the detection signal pulses based on the offset, b) comparing the detection signal pulses with detection signal pulse height thresholds defining energy bins, in order to distribute the detection signal pulses among the energy bins, and c) generating for each energy bin a detection value being indicative of the rate of detection signal pulses of the respective energy bin. This provides a further possibility to correct the detection values depending on the offset in a relatively simple way.

In a further aspect of the present invention an imaging apparatus for imaging an object is presented, wherein the imaging apparatus comprises:

a photon source for generating photons having different energies for traversing the object, a detection apparatus for detecting the photons after having traversed the object and for generating energy-resolved detection values as defined in claim 1. The photon source is preferentially a polychromatic x-ray source and the detection apparatus is preferentially adapted to detect x-ray photons, after having traversed the object. The imaging apparatus is preferentially a computed tomography system or an x-ray C arm system, which allow rotating the photon source and the detection apparatus around the object along a trajectory arranged on, for example, an imaginary cylinder or an imaginary sphere. The trajectory is, for example, a circular or helical trajectory.

The imaging apparatus can comprise a control unit for controlling the photon source and the detection apparatus, wherein the photon source and the detection apparatus are controlled such that the artificial signal pulses are generated and received by the detection values generation unit, when the detection unit does not detect photons. This allows determining the offset, while the detection apparatus is not illuminated by the photons generated by the photon source. This reduces generally possible disturbances in the determination of the offset by the photons and can therefore further improve the reliability of the determination of the offset.

The imaging apparatus comprises preferentially a reconstruction unit for reconstructing an image of the object based on the energy-resolved detection values and the offset. In particular, the reconstruction unit can be adapted to reconstruct an image of the object based on the uncorrected energy-resolved detection values and the offset. The offset can be regarded as being a shift in the detection signal pulse height thresholds of the energy bins. These shifted thresholds can be considered by, for example, a material decomposition technique, which decomposes the detection values into different components, which can be indicative of different materials like bone and soft tissue, and/or different physical effects like the photoelectric effect, the Compton effect and a K-edge effect. A corresponding decomposition technique is disclosed, for example, in the article "K-Edge imaging in x-ray computed tomography using multi-bin photon counting detectors" by E. Roessl and R. Proksa, Physics in Medicine and Biology, volume 52, pages 4679 to 4696 (2007), which is herewith incorporated by reference.

In a further aspect of the present invention a detection method for detecting photons is presented, wherein the detection method comprises:

detecting photons by a detection unit, wherein detection signal pulses having a detection signal pulse height being indicative of the energy of the respective detected photon are generated, generating energy-resolved detection values depending on the detection signal pulses by a detection values generation unit, generating artificial signal pulses having a predefined artificial signal pulse height and a predefined generated rate by a signal pulse generation unit, and providing the generated artificial signal pulses to the detection values generation unit, wherein the detection values generation unit a) receives the artificial signal pulses, b) determines an observed rate being the rate of the received artificial signal pulses having an artificial signal pulse height being larger than a predefined artificial signal height pulse threshold, wherein the artificial signal height pulse threshold is similar or larger than the predefined artificial signal pulse height, and c) determines an offset of the detection signal pulses depending on the determined observed rate of the artificial signal pulses.

In a further aspect of the present invention an imaging method for imaging an object is presented, wherein the imaging method comprises:

generating photons having different energies for traversing the object by a photon source, detecting the photons for generating energy-resolved detection values and determining an offset as defined in claim 12.

In a further aspect of the present invention a detection computer program for detecting energy resolved detection data is presented, wherein the computer program comprises program code means for causing a detection apparatus as defined in claim 1 to carry out the steps of the detection method as defined in claim 12, when the detection computer program is run on a computer controlling the detection apparatus.

In a further aspect of the present invention an imaging computer program for imaging an object is present, wherein the imaging computer program comprises program code means for causing an imaging apparatus as defined in claim 9 to carry out the steps of the imaging method as defined in claim 13, when the imaging computer program is run on a computer controlling the imaging apparatus.

It shall be understood that the detection apparatus of claim 1, the imaging apparatus of claim 9, the detection method of claim 11, the imaging method of claim 13, the detection computer program of claim 14 and the imaging computer program of claim 15 have similar and/or identical preferred embodiments, in particular, as defined in the dependent claims.

It shall be understood that a preferred embodiment of the invention can also be any combination of the dependent claims with the respective independent claim.

These and other aspects of the invention will be apparent from and elucidated with reference to the embodiments described hereinafter.

DETAILED DESCRIPTION OF EMBODIMENTS

Figure 1:
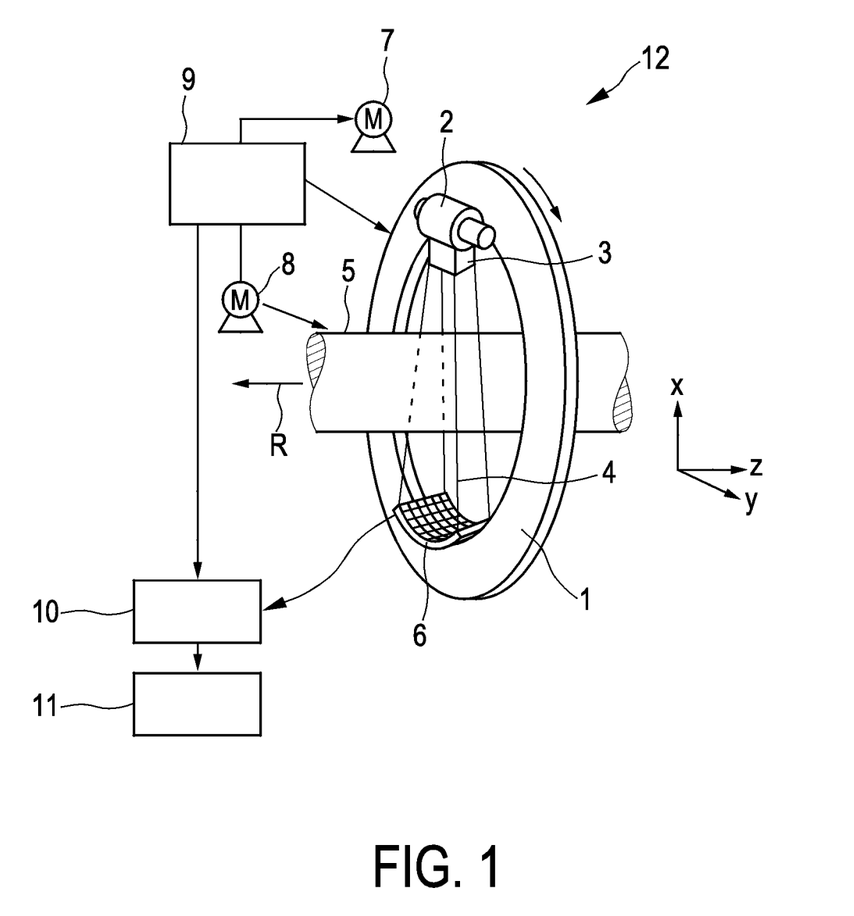
FIG. 1 shows schematically and exemplarily an embodiment of an imaging apparatus for imaging an object.

FIG. 1 shows schematically and exemplarily an imaging apparatus for imaging an object being a computed tomography apparatus 12. The computed tomography apparatus 12 includes a gantry 1, which is capable of rotation about a rotational axis R, which extends parallel to a z direction. A photon source 2, which is, in this embodiment, a polychromatic x-ray tube, is mounted on the gantry 1. The photon source 2 is provided with a collimator 3, which forms, in this embodiment, a conical radiation beam 4 from the photons generated by the photon source 2. The photons traverse an object such as a patient in an examination zone 5, which is, in this embodiment, cylindrical. After having traversed the examination zone 5, the radiation beam 4 is incident on a detection apparatus 6, which comprises a two-dimensional detection surface. The detection apparatus 6 is mounted on the gantry 1.

The computed tomography apparatus 12 comprises two motors 7, 8. The gantry 1 is driven at a preferably constant but adjustable angular speed by the motor 7. The motor 8 is provided for displacing the object, for example, a patient, who is arranged on a patient table in the examination zone 5, parallel to the direction of the rotational axis R or the z axis. These motors 7, 8 are controlled by a control unit 9, for instance, such that the photon source 2 and the examination zone 5 move relative to each other along a helical directory. However, it is also possible that the object is not moved, but that only the photon source 2 is rotated, i.e. that the photon source 2 moves along a circular directory relative to the object or the examination zone 5. Furthermore, in another embodiment, the collimator 3 can be adapted for forming another beam shape, in particular a fan beam, and the detection apparatus 6 can comprise a detection surface, which is shaped corresponding to the other beam shape, in particular to the fan beam.

During a relative movement of the photon source 2 and the examination zone 5, the detection apparatus 6 generates detection values depending on the radiation incident on the detection surface of the detection apparatus 6. The detection values are provided to a reconstruction unit 10 for reconstructing an image of the object based on the detection values. The image reconstructed by the reconstruction unit 10 is provided to a display unit 11 for displaying the reconstructed image.

The control 9 is preferentially also adapted to control the photon source 2, the detection apparatus 6 and the reconstruction unit 10.

Figure 2:
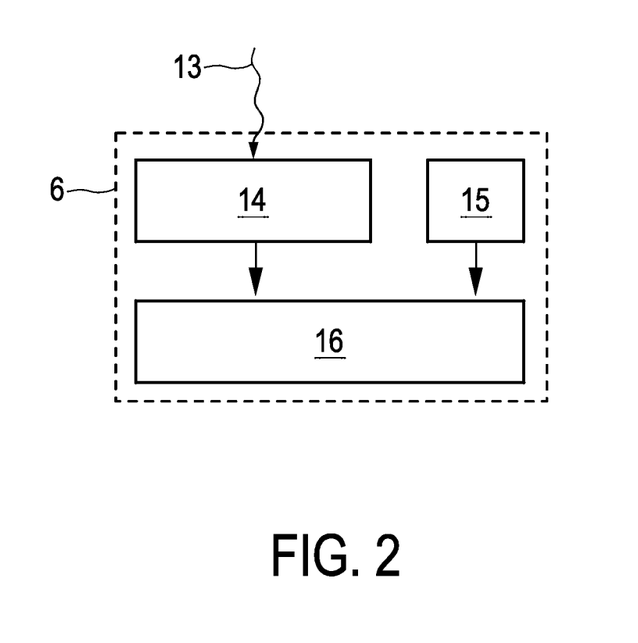
FIG. 2 shows schematically and exemplarily an embodiment of a detection apparatus for detecting photons.

FIG. 2 shows schematically and exemplarily a detection unit 14, a signal pulse generation unit 15 and a detection value generation unit 16 of the detection apparatus 6. The detection unit 14 is adapted to detect photons 13 and to generate detection signal pulses having a detection signal pulse height being indicative of the energy of the respective detected photon 13. The signal pulse generation unit 15 is adapted to generate artificial signal pulses having a predefined artificial signal pulse height and a predefined generated rate, and to provide the generated artificial signal pulses to the detection values generation unit 16. The detection value generation unit 16 is adapted to a) receive the artificial signal pulses, b) determine an observed rate being the rate of the received artificial signal pulses having an artificial signal pulse height being larger than a predefined artificial signal height threshold, wherein the artificial signal height threshold is similar to or larger than the predefined artificial signal pulse height, and c) determine an offset of the detection signal pulses depending on the determined observed rate of the artificial signal pulses.

The detection unit 14 comprises a direct conversion material like CdCe or CZT for generating the detection signal pulses depending on photons 13 meeting the direct conversion material. Such a detection unit comprising a direct conversion material is disclosed, for example, in the article "Recent progress in CdTe and CdZnTe detectors" by T. Takahashi and S. Watanabe, IEEE Transactions on Nuclear Science, volume 48, issue 4, pages 950 to 959, August 2001, which is herewith incorporated by reference.

The signal pulse generator 15 can be a known signal pulse generator like the commercially available signal pulse generator 81130A from the company Agilent Technologies.

The detection values generation unit 16 is adapted to compare the artificial signal pulses with the artificial signal height threshold for determining the observed rate. The detection values generation unit 16 is further adapted to compare the detection signal pulses with detection signal height thresholds defining energy bins, in order to distribute the detection signal pulses among the energy bins, wherein for each energy bin a detection value is determined being indicative of the rate of detection signal pulses assigned to the respective energy bin. The comparison procedures for comparing the detection signal pulses and the artificial signal pulses with respective thresholds are performed by comparators of the detection values generation unit 16. The observed rate is a rate of the artificial signal pulses having an artificial signal pulse height larger than the artificial signal height threshold, when the artificial signal pulse heights are compared with the artificial signal height threshold in the detection values generation unit 16 by using the comparators. The generated rate refers to a predefined rate of the artificial signal pulses as generated by the signal pulse generation unit 15.

The detection signal pulse heights are smaller than a predefined maximal detection signal pulse height, and the artificial signal height threshold is larger than the maximal detection signal pulse height.

The detection values generation unit 16 comprises assignments between observed rates and the offsets, wherein the detection values generation unit 6 is adapted to determine the offset based on the assignments and the actual observed rate.

The assignments can be determined by calibration measurements, wherein the observed rate is determined, while the offset is known and also the predefined generated artificial signal pulses, i.e. their generated artificial signal pulse heights and the generated rate, are known. The assignments can also be provided based on a function between the observed rate and the offset, which may be based on theoretical considerations. In particular, the detection values generation unit 6 can be adapted to provide a model modeling the observed rate $R_O$ as a product of a) the generated rate $R_G$ of artificial signal pulses and b) a noise likelihood P defining the likelihood that the noise in the artificial signal pulses is larger than the artificial signal height threshold $V_T$ minus a generated artificial pulse height $V_P$ and minus the offset $V_B$. This modeling of the observed rate $R_O$ can be described by following equations:

$$V_N = V_T - V_P - V_B \text{ and} \quad (1)$$

$$R_O = R_G P \quad (2)$$

The likelihood P can be determined by integrating a corresponding likelihood density like a Gaussian likelihood density from the artificial signal height threshold $V_T$ minus a generated artificial pulse height $V_P$ and minus the offset $V_B$ to infinity. A resulting Gaussian probability can exemplarily be described by following equation:

$$P = \frac{1}{\sigma_N \sqrt{2\pi}} \int_{V_N}^{\infty} e^{-0.5\left(\frac{V}{\sigma_N}\right)^2} dV. \quad (3)$$

In equation (3), a zero mean electronic noise with a Gaussian shape has been assumed, wherein $\sigma_N$ denotes the noise variance. The noise variance of the detection apparatus, in particular, of the detection values generation unit can be measured in advance in a known way.

The detection values generation unit 6 can be adapted to modify the offset $V_B$ such that deviations between the modeled observed rate and an actually observed rate, which has actually been measured, are reduced, thereby determining the offset.

The detection values generation unit can be adapted to provide a pile-up model modeling a pile-up effect caused by combined detection signal and artificial signal pulses having a combined signal pulse height being larger than the artificial signal height threshold and to correct the observed rate of artificial signal pulses with artificial signal pulse heights being larger than the artificial signal height threshold based on the pile-up model.

If it is assumed that the photons will have a Poisson distributed arrival at the detection unit with input count rate $R_{ICR}$, the likelihood $P_P$ of pile-up of artificial signal pulses with detection signal pulses, which are generated based on the incoming photons, can be defined by following equation:

$$P_P = 1 - e^{(-R_{ICR}\tau)}, \quad (4)$$

wherein $\tau$ denotes the time period, in which the determination of the observed rate of the artificial signal pulses is sensitive to pile-up. This time period can be determined in advance by calibration measurements. The observed rate of artificial signal pulses including the rate originated by pile-up $\tilde{R}_O$ contains the pile-up free rate $R_O$ and the pile-up related rate $P_P(R_G - R_O)$. The pile-up free rate can by estimated by $$R_O = \frac{\tilde{R}_O - P_P R_G}{1 - P_P}. \quad (5)$$

Thus, the detection values generation unit can be adapted to correct the observed rate of artificial signal pulses with artificial signal pulse heights being larger than the artificial signal height threshold in accordance with equation (5).

The detection values generation unit 16 is further adapted to generate the energy-resolved detection values by a) comparing the detection signal pulses with detection signal height thresholds defining energy bins, in order to distribute the detection signal pulses among the energy bins, b) correcting the distribution of detection signal pulses based on the offset, and c) generating for each energy bin a detection value being indicative of the rate of detection signal pulses of the respective energy bin. In particular, the detection values generation unit 16 is adapted to determine a sensitivity of a rate of detection signal pulses assigned to a respective energy bin on the offset and to correct the rate of detection signal pulses assigned to the respective energy bin based on the offset and the determined sensitivity. The rate of detection signal pulses assigned to a respective energy bin can be corrected based on a product of the offset $V_B$ and the sensitivity $S_i$, of the rate of detection signal pulses assigned to the respective energy bin, which is denoted by the index i, on the offset. Such a correction can be exemplarily described by following equation:

$$\tilde{C}_i = C_i + V_B S_i, \quad (6)$$

wherein $C_i$ denotes the rate of detection signal pulses assigned to the i-th energy bin before correction, $\tilde{C}_i$ denotes the rate of detection signal pulses assigned to the i-th energy bin after correction and $S_i$ denotes the sensitivity of the rate of detection signal pulses assigned to the i-th energy bin on the offset $V_B$.

The sensitivity $S_i$ can be defined by following equation:

$$S_i = D(T_{i+1}) - D(T_i) \text{ with} \quad (7)$$

$$D(T_i) = \begin{cases} C_0/(T_1 - T_0) & i = 0 \\ 0.5\left(\frac{C_{i-1}}{T_i - T_{i-1}} + \frac{C_i}{T_{i+1} - T_i}\right) & 0 < i < N_T - 1 \\ 0 & i = N_T - 1 \end{cases} \quad (8)$$

wherein $T_i$ and $T_{i+1}$ denote first and second detection signal pulse height thresholds of the i-th energy bin, $N_T$ is a number of detection signal pulse height thresholds and i=0, 1, 2 . . . $N_T-1$. The values $D(T_i)$ can be regarded as being pulse rate densities given for some discrete $T_i$.

The sensitivity of the rate of detection signal pulses assigned to a respective energy bin on the offset can therefore be determined based on an average of a) a ratio of the rate of detection signal pulses assigned to a respective energy bin to the width of the respective energy bin, and b) a ratio of the rate of detection signal pulses assigned to an adjacent energy bin to the width of the adjacent energy bin.

In another embodiment the pulse rate density $D(T_i)$ can also be defined by following equation:

$$D(T_i) = \frac{R_i - R_{\Delta i}}{T_i - T_{\Delta i}}. \quad (9)$$

In equation (9), the rate of detection signal pulses having detection signal pulse heights being larger than the detection signal pulse height threshold $T_i$ is denoted by $R_i$ and the rate of detection signal pulses having detection signal pulse heights being larger than a sensitivity signal pulse height threshold $T_{\Delta i}$, which is smaller than the respective detection signal pulse height threshold $T_i$, is denoted by $R_{\Delta i}$. The sensitivity of the respective energy bin, which considers the pulse rate densities at the corresponding two signal pulse height detection thresholds, i.e. a first detection signal pulse threshold and a second detection signal pulse threshold, can then be determined as follows.

The rate of detection signal pulses of the respective energy bin can be determined as a difference between a) a first rate being the rate of detection signal pulses having detection signal pulse heights being larger than the first detection signal height pulse threshold and b) a second rate being the rate of detection signal pulses having detection signal pulse heights being larger than the second detection signal height pulse threshold. A third rate being the rate of detection signal pulses having a detection signal pulse height being larger than a first sensitivity signal height pulse threshold, which is smaller than the first detection signal pulse height threshold, is determined. A fourth rate being the rate of detection signal pulses having detection signal pulse heights being larger than a second sensitivity signal pulse height threshold, which is smaller than the second detection signal pulse height threshold, is determined. A first pulse rate density for the respective energy bin is then determined by subtracting the first and third rates from each other and by dividing the subtraction result by the difference between the first detection signal height pulse threshold and the first sensitivity signal height pulse threshold. A second pulse rate density can be determined by subtracting the second and fourth rates from each other and dividing the subtraction result by the difference between the second detection signal pulse threshold and the second sensitivity signal pulse height threshold. The sensitivity of the respective energy bin on the offset can then be defined as the difference between the first and second pulse rate densities, which have been determined for this energy bin.

The above described correction of the rate of detection signal pulses assigned to a respective energy bin is based on the insight that an offset in the detection signal pulse heights can be regarded as a shift of the first and second detection signal pulse height thresholds of the respective energy bin. The correction, which results from this insight, will in the following be illustrated with reference to FIG. 3.

Figure 3:
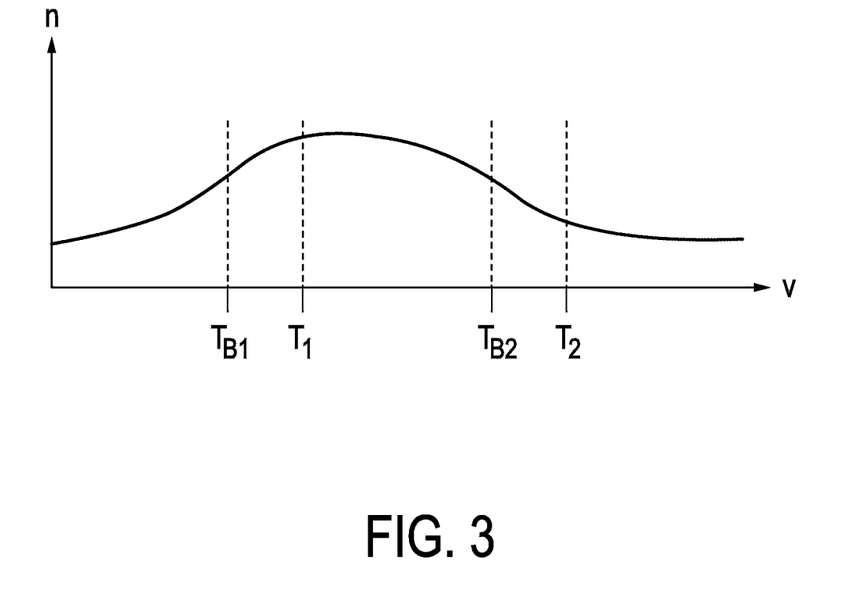
FIG. 3 shows schematically and exemplarily a spectrum of photons.

FIG. 3 shows the distribution n of detection signal pulses over the detection signal pulse heights V. The detection signal pulse height thresholds for a respective energy bin are denoted by $T_1$ and $T_2$. All detection signal pulses having detection signal pulse heights between the detection signal pulse height thresholds $T_1$ and $T_2$ should be assigned to the respective energy bin. However, due to the offset, the thresholds $T_1$ and $T_2$ are shifted to the thresholds $T_{B1}$ and $T_{B2}$. The uncorrected rate, which has originally been assigned to the respective energy bin, corresponds therefore to the detection signal pulses having detection signal heights between the shifted thresholds $T_{B1}$ and $T_{B2}$. In order to correct the rate of detection pulse signals assigned to the respective energy bin, from the originally assigned rate the rate between the thresholds $T_{B1}$ and $T_1$ has to be subtracted and the rate between the thresholds $T_{B2}$ and $T_2$ has to be added to the originally assigned rate. This correction is reflected by equations (6) and (7).

In another embodiment, the detection values generation unit can also be adapted to generate the energy-resolved detection values by a) correcting the detection signal pulses based on the offset, b) comparing the detection signal pulses with detection signal pulse height thresholds defining energy bins, in order to distribute the detection signal pulses among the energy bins, and c) generating for each energy bin a detection value being indicative of the rate of detection signal pulses of the respective energy bin. In particular, before distributing the detection signal pulses among the energy bins, the offset can be subtracted from the detection signal pulse heights.

The control unit 9 can be adapted such that the photon source 2 and the detection apparatus 6 are controlled in a way that the artificial signal pulses are generated and received by the detection values generation unit 16 only, when the detection unit 14 does not detect photons. In particular, the photon source 2 can be an x-ray tube with a grid switch electrode, wherein the grid switch can be used to block a photon flux from the x-ray tube for bias measurements, i.e. for determining the offset. These bias measurements can be inserted into an imaging sequence to monitor the bias drift, i.e. the offset. For example, immediately before, immediately after or between two radiation periods, in which photons, which have traversed the object, are detected, the bias measurement can be performed. In another embodiment, instead of an x-ray tube with the grid switch electrode, another mechanism can be used for temporarily switching the photon source off. For example, the photon source can be a standard x-ray tube, which can be switched on and off. Or, a shutter can be used in front of the photon source, which allows temporarily blocking the photon flux for performing the bias measurement. If the photon flux can be stopped, in order to perform the bias measurement, no additional threshold unit is required to perform the bias measurement, but a regular threshold/counter pair, which is used to define the energy bins, among which the detection signal pulses are distributed, can be reprogrammed to perform the bias measurement. Multiple pairs can be used to extend the range of the bias measurement and/or to increase the accuracy.

In another embodiment, the detection values generation unit just distributes the detection signal pulses among the energy bins, without correcting this distribution with respect to the offset. Instead, the reconstruction unit 10 is adapted to consider shifted detection signal pulse height thresholds, which can be regarded as being shifted by the determined offset, while reconstructing an image of the object based on the uncorrected energy-resolved detection values. For instance, the reconstruction unit 10 can be adapted to decompose the detection values into different component detection values, which correspond to different components of the object. These different components are, for example, related to different physical effects like the Compton effect, the photoelectric effect and a K-edge effect, and/or the different components can be related to different materials like bone, soft tissue, et cetera of a human being. For instance, the reconstruction unit can use the decomposition technique disclosed in the article "K-Edge imaging in x-ray computed tomography using multi-bin photon counting detectors" by E. Roessl and R. Proksa, Physics in Medicine and Biology, Volume 52, pages 4679 to 4696 (2007), which is herewith incorporated by reference.

In an embodiment, the decomposition is performed in accordance with following equation, which is based on the inversion of a physical model describing the measurement process:

$$C_i = \int_{TE_i}^{TE_{i+1}} B_i(E)F(E)e^{-\sum_j^{M_j} A_j P_j(E)} dE, \qquad (10)$$

wherein $C_i$ denotes the uncorrected rate of detection signal pulses in the i-th energy bin, $B_i(E)$ denotes the spectral sensitivity of the i-th energy bin, $F(E)$ denotes the spectrum of the photon source, j is an index for the $M_j$ different components, $A_j$ denotes a line integral of absorption values through the j-th component and $P_j(E)$ denotes the spectral absorption of the j-th component. The thresholds $TE_i$ and $TE_{i+1}$ define the i-th energy bin and are shifted in accordance with the determined offset, i.e. the determined offset of the detection signal pulse heights corresponds to a shift of the energy thresholds defining an energy bin. If this determined energy shift is $\Delta E$ and if, without considering the shift, the thresholds are $TW_i$ and $TW_{i+1}$, respectively, the shifted thresholds can be defined by $TE_i = TW_i - \Delta E$ and $TE_{i+1} = TW_{i+1} - \Delta E$. Since the model can be applied to each measurement individually, for each measurement an individual bias can be used.

If the number of energy bins is at least equal to the number of components, the system of equations can be solved with known numerical methods, wherein the quantities $B_i(E)$, $F(E)$ and $P_j(E)$ are known and the results of solving the system of equations are the line integrals $A_j$. The spectrum of radiation $F(E)$ and the spectral sensitivity $B_i(E)$ are characteristics of the imaging system and are known from, for example, corresponding measurements. The spectral absorption $P_j(E)$ of the components, for example, the spectral absorption of bone and soft tissue, is also known from measurements and/or from literature.

The decomposed detection values are, in this embodiment, decomposed projection data, i.e. the line integrals $A_j$ which can each be used for reconstructing a computed tomography image of the object such that, for instance, for each component a component image of the object can be reconstructed. For instance, a Compton component image, a photoelectric component image and/or a K-edge component image can be reconstructed. For reconstructing an image based on the projection data known reconstruction techniques can be used like filtered back projection, Radon inversion, et cetera.

Figure 4:
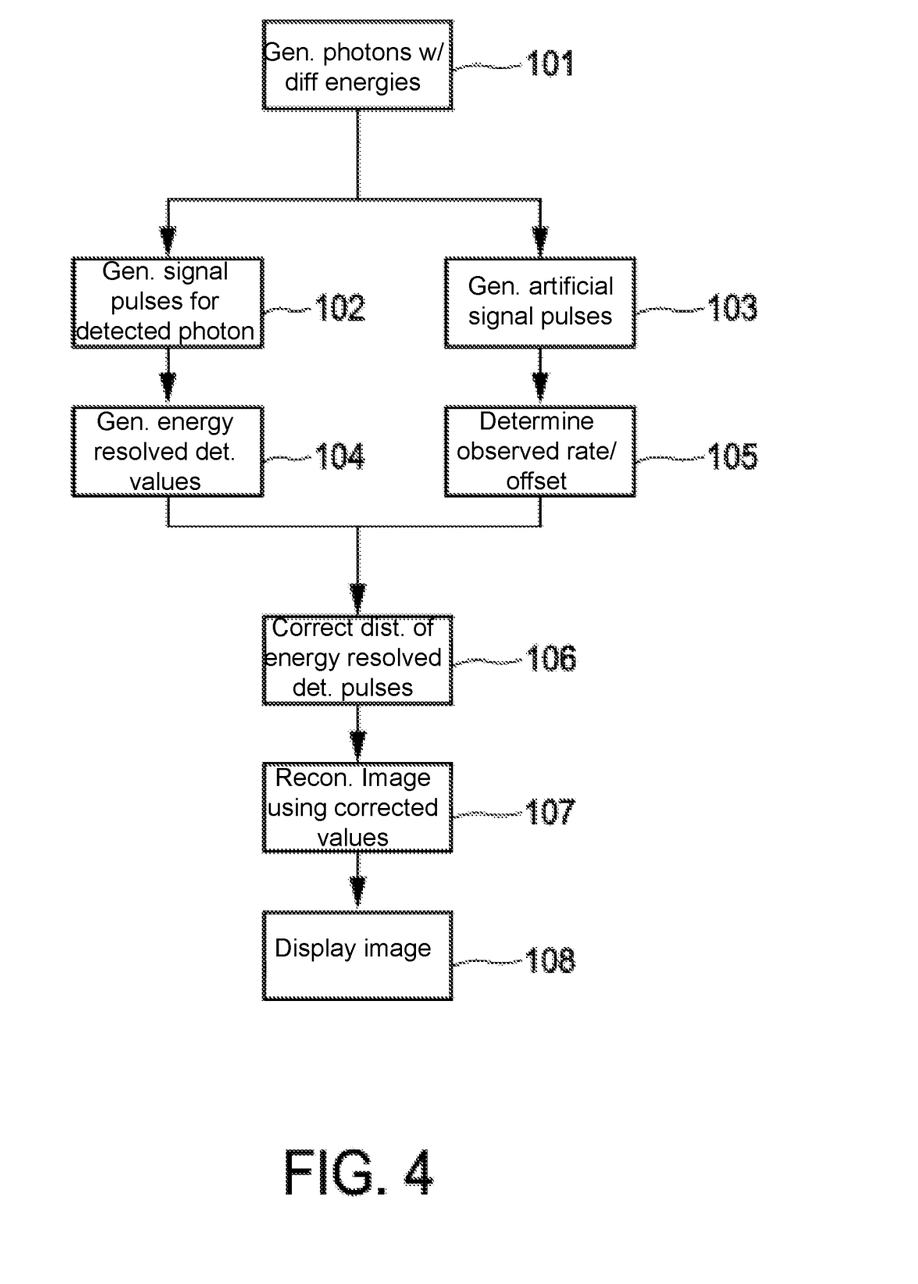
FIG. 4 shows a flowchart exemplarily illustrating an embodiment of an imaging method for imaging an object.

In the following an embodiment of an imaging method for imaging an object will exemplarily be described with reference to a flowchart shown in FIG. 4.

In step 101, the photon source 2 generates photons having different energies, while the photon source 2 and the object are moved relatively to each other, in order to allow the photons to traverse the object in different directions. In particular, the photon source 2 is moved along a circular or helical trajectory around the object, while the detection unit 14 detects the photons, which have traversed the object.

In step 102, the detection unit 14 generates detection signal pulses having a detection signal pulse height being indicative of the energy of the respective detected photon. For instance, a direct conversion material can be used for transforming the respective photon into a detection signal pulse having a detection signal pulse height being indicative of the energy of the respective detected photon. Before, during or after the generation of the detection signal pulses, in step 103 the signal pulse generation unit 15 generates artificial signal pulses having a predefined artificial signal pulse height and a predefined generated rate, wherein the generated artificial signal pulses are provided to the detection values generation unit 16. Also the detection signal pulses are provided to the detection values generation unit 16.

In step 104, the detection values generation unit 16 generates energy-resolved detection values depending on the received detection signal pulses. In particular, the detection signal pulse heights of the detection signal pulses are compared with detection signal height pulse thresholds defining energy bins, in order to distribute the detection signal pulses among the energy bins. Since the detection signal pulses are likely to be corrupted by an offset, which may be caused by persistent currents, when comparing the detection signal pulse heights with the detection signal pulse height thresholds, the quality of the distribution of the detection signal pulses among the energy bins and, thus, of the generated energy-resolved detection values can be reduced.

In step 105, the detection values generation unit 16 determines an observed rate being the rate of the received artificial signal pulses having an artificial signal pulse height being larger than a predefined artificial signal height threshold, wherein the artificial signal height threshold is similar to or larger than the predefined artificial signal pulse height. Moreover, in this embodiment the predefined artificial signal pulse height is larger than the largest expected detection signal pulse height as defined by the maximal possible energy of the photons generated by the photon source in accordance with the actual operating settings of the photon source. The detection values generation unit determines then an offset of the detection signal pulse heights depending on the determined observed rate of the artificial signal pulses.

In step 106, the distribution of the detection signal pulses among the energy bins is corrected by using the determined offset for generating corrected energy-resolved detection values. In step 107, the reconstruction unit 10 reconstructs an image of the object based on the corrected energy-resolved detection values by using, for example, computed tomography reconstruction algorithms like a filtered backprojection algorithm, wherein in step 108 the image is shown on the display unit 11.

Steps 102 to 106 can be regarded as being the steps of a detection method for detecting photons.

Although in the embodiment of the imaging method described above with reference to FIG. 4 the imaging method comprises a certain sequence of steps, in other embodiments the sequence of steps can be different. In particular, in other embodiments the sequence can comprise other steps. For instance, the generation of the artificial signal pulses and the determination of the offset based on the artificial signal pulses can be performed, while the detection unit does not detect photons. Moreover, in an embodiment the detection values are not corrected based on the offset, but the reconstruction unit considers the offset by performing the reconstruction with shifted detection signal pulse height thresholds based on the generated detection values, wherein the shift is caused by the offset.

Photon counting detector can have Ohmic contacts and suffer from varying persistent currents. Several physical effects in a direct conversion material like CdCe or CZT can cause the variation of this very low frequency current. In the electronics of the detection apparatus this current has the effect of and can be modeled as a bias or direct current (DC) offset. A DC offset can virtually be regarded as a shift of the thresholds for the energy bins and can cause a severe distortion of the acquired information. The imaging apparatus, in particular, the detection apparatus, is therefore preferentially adapted to measure the persistent current related bias component, i.e. the offset, to measure the sensitivity, i.e. the potential impact, to the bias component, and to perform a correction of the acquired data, i.e. a correction of the distribution of the detection signal pulses among the energy bins.

The detection apparatus has preferentially means to add electronic pulses, i.e. the signal pulse generation unit for generating the artificial signal pulses, with a well-defined charge and repetition frequency to the input of the front-end electronics, i.e. to the input of the detection values generation unit. The effective energy of these electronic pulses is preferentially higher than the maximal photon energy provided by the photon source in the respective imaging procedure. A threshold/counter pair can be used to count these electronic pulses. The threshold is preferentially selected such that it is just above the effective energy, i.e. the predefined generated artificial signal pulse height, of the electronic pulses. Without a bias in the signal, the counter would count no or very little signal pulses, i.e. only if the noise on top of the pulse is high enough to reach the respective threshold. With an increasing bias, more and more pulses will reach the threshold and generate counts. The number of recorded counts can therefore be regarded as being an indicator of the bias, i.e. of the offset. Based on calibration or theoretical considerations the bias can be estimated, given the recorded counts in this threshold/counter pair. A possible influence by a pile-up with detection signal pulses generated by a direct conversion material of the detection unit can be ignored, corrected based on a pile-up model or the photon flux may be stopped during the measurement, in order to avoid the pile-up effect.

Knowing the bias can directly lead to a correction step, but it can also be advantageous to measure the sensitivity of an energy bin to a bias. Referring again to FIG. 3, which shows an exemplarily spectrum and one energy bin bounded with thresholds $T_1$ and $T_2$, a bias, i.e. an offset, can virtually shift these thresholds to $T_{B1}$ and $T_{B2}$. This shift can cause that photons in the interval $[T_{B1}, T_1]$ can erroneously be counted while photons in the interval $[T_{B2}, T_2]$ are not counted. These additional counts and losses can be estimated, if, for example, the pulse rate around $T_1$ and $T_2$ and the bias are known. A good estimation of the pulse rate density close to a threshold can be derived from an additional measurement with a threshold/counter pair for which the threshold is close to $T_1$ or $T_2$, respectively. In particular, the pulse rate density at a threshold $T_i$ and can be estimated in accordance with equation (9).

In an embodiment, the detection apparatus is based on the photon-counting detector described in the above mentioned article by X. Llopart et al., wherein an additional signal pulse generator for generating the artificial signal pulses inputs the artificial signal pulses to the input of the electronics of the detector, which compare the signals with thresholds and count the signals for generating the detection values and which can therefore be regarded as being at least a part of a detection values generation unit. The detection values generation unit can further comprise a computing unit like a microcontroller for controlling the detection apparatus and/or for performing calculations, in particular, in accordance with the above described equations.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Operations like the comparing operations, the determination of the offset, the correction of the detection values, i.e. of the distribution of the detection signal pulses among the energy bins, the reconstruction operation, et cetera performed by one or several units or devices can be performed by any other number of units or devices. These operations and/or the control of the imaging apparatus in accordance with the imaging method and/or the control of the detection apparatus in accordance with the detection method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a detection apparatus for detecting photons. A detection unit generates detection signal pulses having a detection signal pulse height being indicative of the energy of the detected photons, wherein a detection values generation unit generates energy-resolved detection values depending on the detection signal pulses. A signal pulse generation unit generates artificial signal pulses having a predefined artificial signal pulse height and a predefined generated rate. The detection values generation unit determines an observed rate being the rate of the artificial signal pulses having an artificial signal pulse height being larger than a predefined threshold as observed by the detection values generation unit and determines an offset of the detection signal pulses depending on the determined observed rate. This allows reliably determining the offset of the detection signal pulses, which can be used for correcting the finally generated detection values.

The invention claimed is:

1. A detection apparatus for detecting photons, the detection apparatus comprising:
    a detection unit for detecting photons, wherein the detection unit is adapted to generate detection signal pulses having a detection signal pulse height being indicative of the energy of the respective detected photon;
    a detection values generation unit for generating energy-resolved detection values depending on the detection signal pulses;
    a signal pulse generation unit for generating artificial signal pulses having a predefined artificial signal pulse height and a predefined generated rate and for providing the generated artificial signal pulses to the detection values generation unit;
    wherein the detection values generation unit is adapted to
    a) receive the artificial signal pulses, b) determine an observed rate being a rate of the received artificial signal pulses having an artificial signal pulse height being larger than a predefined first threshold, wherein the predefined first threshold is larger than the predefined artificial signal pulse height, and c) determine an offset to the indicated energies of the detection signal pulses depending on the determined observed rate of the artificial signal pulses.

2. The detection apparatus as defined in claim 1, wherein the detection signal pulse heights are smaller than a predefined maximal detection signal pulse height and wherein the predefined first threshold is larger than the maximal detection signal pulse height.

3. The detection apparatus as defined in claim 1, wherein the detection values generation unit comprises assignments between observed rates and the offset;
    wherein the detection values generation unit is adapted to determine the offset based on the assignments and an actual observed rate.

4. The detection apparatus as defined in claim 1, wherein the detection values generation unit is adapted to
    provide a model modeling the observed rate as a product of a) the generated rate of artificial signal pulses and b) a noise likelihood defining the likelihood that a noise in the artificial signal pulses is larger than the predefined first threshold minus a generated artificial pulse height and minus the offset;
    modify the offset to be determined such that deviations between the modeled observed rate and an actual observed rate are reduced, thereby determining the offset.

5. The detection apparatus as defined in claim 1, wherein the detection values generation unit is adapted to generate the energy-resolved detection values by comparing the detection signal pulses with detection signal height pulse thresholds defining energy bins, in order to distribute the detection signal pulses among the energy bins, and to correct the distribution of detection signal pulses based on the offset, thereby generating for each energy bin a corrected detection value being indicative of a rate of detection signal pulses of the respective energy bin.

6. The detection apparatus as defined in claim 5, wherein the detection values generation unit is adapted to determine a sensitivity of a rate of detection signal pulses assigned to a first energy bin of said energy bins on the offset and to correct the rate of detection signal pulses assigned to the first energy bin based on the offset and the determined sensitivity.

7. The detection apparatus as defined in claim 6, wherein the first energy bin is defined by two detection signal pulse thresholds, a first detection signal threshold and a second detection signal threshold, wherein the detection values generation unit is adapted to
- determine the rate of detection signal pulses of an energy bin as the difference between a) a first rate being the rate of detection signal pulses having detection signal pulse heights being larger than the first detection signal threshold and b) a second rate being the rate of detection signal pulses having detection signal pulse heights being larger than the second detection signal threshold,
- determine a third rate being the rate of detection signal pulses having a detection signal pulse height being larger than a first sensitivity signal threshold, which is smaller than the first detection signal threshold,
- determine a fourth rate being the rate of detection signal pulses having detection signal pulse heights being larger than a second sensitivity signal threshold, which is smaller than the second detection signal threshold,
- determine the sensitivity of the rate of detection signal pulses assigned to the first energy bin on the offset depending on a difference between the first and third rates and a difference between the second and fourth rates.

8. The detection apparatus as defined in claim 6, wherein the detection values generation unit is adapted to determine the sensitivity of a rate of detection signal pulses assigned to a respective energy bin of the energy bins on the offset based on an average of a) a ratio of the rate of detection signal pulses assigned to the respective energy bin to a width of the respective energy bin and b) a ratio of the rate of detection signal pulses assigned to an adjacent energy bin to the width of the adjacent energy bin.

9. An imaging apparatus for imaging an object, the imaging apparatus comprising:
- a photon source for generating photons having different energies for traversing the object,
- a detection apparatus for detecting the photons after having traversed the object and for generating energy-resolved detection values as defined in claim 1.

10. The imaging apparatus as defined in claim 9, wherein the imaging apparatus further comprises a control unit for controlling the photon source and the detection apparatus, wherein the photon source and the detection apparatus are controlled such that the artificial signal pulses are generated and received by the detection values generation unit, when the detection unit does not detect photons.

11. The imaging apparatus as defined in claim 9, wherein the imaging apparatus further comprises a reconstruction unit for reconstructing a computed tomography (CT) image of the object based on the energy-resolved detection values with the offset applied.

12. The detection apparatus as defined in claim 1, wherein the detected photons are polychromatic x-ray photons.

13. The detection apparatus as defined in claim 1, wherein the detection unit for detecting photons includes a direct conversion material which includes at least one of CdCe or CZT to generate the detection signal pulses having the detection signal pulse height being indicative of the energy of the respective detected photon.

14. The detection apparatus as defined in claim 1, wherein the offset to the indicated energy determined by the observed rate is based on calibration measurements which assigns offsets to observed rates.

15. The detection apparatus as defined in claim 1, wherein the offset to the indicated energy determined by the observed rate is based on a modeled function of the observed rate.

16. A detection method for detecting photons, the detection method comprising:
- detecting photons by a detection unit, wherein detection signal pulses having a detection signal pulse height being indicative of the energy of the respective detected photon are generated,
- generating energy-resolved detection values depending on the detection signal pulses by a detection values generation unit,
- generating artificial signal pulses having a predefined artificial signal pulse height and a predefined generated rate by a signal pulse generation unit, and providing the generated artificial signal pulses to the detection values generation unit,
- wherein the detection values generation unit a) receives the artificial signal pulses, b) determines an observed rate being a rate of the received artificial signal pulses having an artificial signal pulse height being larger than a predefined first threshold, wherein the predefined first threshold is larger than the predefined artificial signal pulse height, and c) determines an offset to the indicated energies of the detection signal pulses depending on the determined observed rate of the artificial signal pulses.

17. An imaging method for imaging an object, the imaging method comprising:
- generating photons having different energies for traversing the object by a photon source,
- detecting the photons for generating energy-resolved detection values and determining an offset as defined in claim 16.

18. A non-transitory storage media comprising program code for causing an imaging apparatus to carry out the steps of the imaging method as defined in claim 17, wherein the program code is run on a computer controlling the imaging apparatus.

19. A non-transitory storage media comprising program code for causing a detection apparatus to carry out the steps of the detection method as defined in claim 16, wherein the program code is run on a computer controlling the detection apparatus.

* * * * *